United States Patent [19]

Bundy

[11] 4,145,534

[45] Mar. 20, 1979

[54] 9-DEOXY-9-METHYLENE-PFG$_1$-PIPERIDYLAMIDES

[75] Inventor: Gordon L. Bundy, Portage, Mich.

[73] Assignee: The Upjohn Company, Kalamazoo, Mich.

[21] Appl. No.: 894,214

[22] Filed: Apr. 7, 1978

Related U.S. Application Data

[63] Continuation-in-part of Ser. No. 786,250, Apr. 11, 1977, Pat. No. 4,098,805.

[51] Int. Cl.$^2$ ............... C07C 177/00; C07D 211/16; C07D 211/34
[52] U.S. Cl. ................... 542/426; 542/429; 546/226

[58] Field of Search ............... 544/426, 429; 260/293.65, 293.8, 293.81, 293.83

[56] References Cited

PUBLICATIONS

Derwent Abstract 16389U-B, NL 7211860-Q, 05-03-73.
Derwent Abstract 75530x/40, U.S. 3981 868, 21-09-76.

*Primary Examiner*—Paul J. Killos
*Attorney, Agent, or Firm*—Robert A. Armitage

[57] ABSTRACT

The present invention relates to novel 9-deoxy-9-methylene-PGF$_1$-piperidylamides. These compounds are useful pharmacological agents, and are useful for the same purposes as the corresponding 9-deoxy-9-methylene-PGF-type acids.

32 Claims, No Drawings

9-DEOXY-9-METHYLENE-PFG$_1$-PIPERIDYLAMIDES

CROSS REFERENCE TO RELATED APPLICATIONS

This application is a continuation-in-part of Ser. No. 786,250, filed Apr. 11, 1977, now U.S. Pat. No. 4,098,805, issued July 4, 1978.

The present application is a continuation-in-part of Ser. No. 786,250, filed Apr. 11, 1977, now U.S. Pat. No. 4,098,805. The present invention relates to novel 9-deoxy-9-methylene-PGF$_1$-piperidylamides, the essential material constituting a disclosure of which is incorporated here by reference from U.S. Pat. No. 4,098,805.

I claim:

1. A prostaglandin analog of the formula

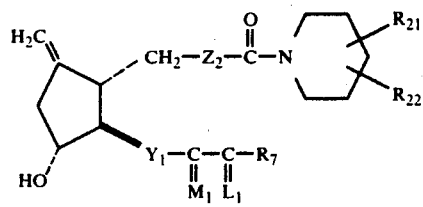

wherein $Y_1$ is trans—CH=CH—, —C≡C—, or —CH$_2$CH$_2$—
wherein $M_1$ is

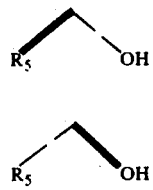

or

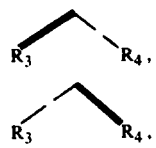

wherein $R_5$ is hydrogen or methyl;
wherein $L_1$ is

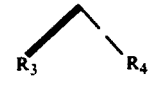

or a mixture of

and wherein $R_3$ and $R_4$ are hydrogen, methyl, or fluoro, being the same or different, with the proviso that one of $R_3$ and $R_4$ is fluoro only when the other is hydrogen or fluoro;
wherein $Z_2$ is
(1) —(CH$_2$)$_3$—(CH$_2$)$_g$—CH$_2$—,
(2) —(CH$_2$)$_3$—(CH$_2$)$_g$—CF$_2$—,
(3) —CH$_2$—O—CH$_2$—(CH$_2$)$_g$—CH$_2$—,
(4) —C≡C—CH$_2$—(CH$_2$)$_g$—CH$_2$—,
(5) —CH$_2$—C≡C—(CH$_2$)$_g$—CH$_2$—,

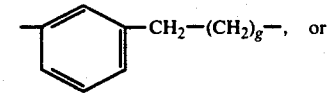

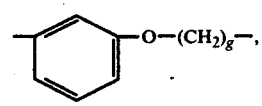

wherein g is one, 2 or 3;
wherein $R_7$ is
(1) —(CH$_2$)$_m$—CH$_3$,

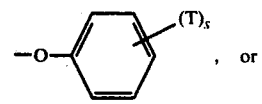

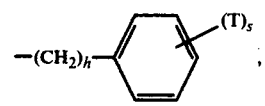

wherein m is one to 5, inclusive, h is zero or one, T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $R_7$ is

wherein T and s are as defined above, only when $R_3$ and $R_4$ are hydrogen or methyl, being the same or different; and wherein $R_{21}$ and $R_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive.

2. A prostaglandin analog according to claim 1, wherein $Y_1$ is —C≡C—.

3. 9-Deoxy-9-methylene-13,14-didehydro-PGF$_1$, piperidylamide, a prostaglandin analog according to claim 2.

4. A prostaglandin analog according to claim 1, wherein $Y_1$ is —CH$_2$CH$_2$—.

5. 9-Deoxy-9-methylene-13,14-dihydro-PGF$_1$, piperidylamide, a prostaglandin analog according to claim 4.

6. A prostaglandin analog according to claim 1, wherein $Y_1$ is trans—CH=CH—.

7. A prostaglandin analog according to claim 6, wherein $Z_2$ is aromatic.

8. 9-Deoxy-9-methylene-3,7-inter-m-phenylene-3-oxa-4,5,6-trinor-PGF$_1$, piperidylamide, a prostaglandin analog according to claim 7.

9. 9-Deoxy-9-methylene-3,7-inter-m-phenylene-4,5,6-trinor-PGF$_1$, piperidylamide, a prostaglandin analog according to claim 7.

10. A prostaglandin analog according to claim 6, wherein Z$_2$ is aliphatic.

11. A prostaglandin analog according to claim 10, wherein M$_1$ is

12. 15-epi-9-deoxy-9-methylene-PGF$_1$, piperidylamide, a prostaglandin analog according to claim 11.

13. A prostaglandin analog according to claim 10, wherein M$_1$ is

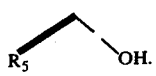

14. A prostaglandin analog according to claim 13, wherein Z$_2$ is cis—CH=CH—CH$_2$—(CH$_2$)$_g$—CH$_2$—.

15. A prostaglandin analog according to claim 14, wherein R$_7$ is

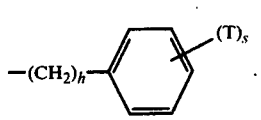

16. 9-Deoxy-9-methylene-17-phenyl-18,19,20-trinor-PGF$_1$, piperidylamide, a prostaglandin analog according to claim 15.

17. A prostaglandin analog according to claim 14, wherein R$_7$ is

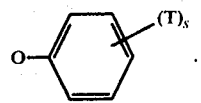

18. 9-Deoxy-9-methylene-16-phenoxy-17,18,19,20-tetranor-PGF$_1$, piperadylamide, a prostaglandin analog according to claim 17.

19. A prostaglandin analog according to claim 14, wherein R$_7$ is —(CH$_2$)$_m$—CH$_3$.

20. A prostaglandin analog according to claim 19, wherein m is 3.

21. A prostaglandin analog according to claim 20, wherein g is 3.

22. 2a,2b-Dihomo-9-deoxy-9-methylene-15-methyl-PGF$_1$, piperadylamide, a prostaglandin analog according to claim 21.

23. A prostaglandin analog according to claim 20, wherein g is one.

24. A prostaglandin analog according to claim 23, wherein at least one of R$_3$ and R$_4$ is methyl.

25. 9-Deoxy-9-methylene-16,16-dimethyl-PGF$_1$, piperadylamide, a prostaglandin analog according to claim 24.

26. A prostaglandin analog according to claim 23, wherein at least one of R$_3$ and R$_4$ is fluoro.

27. 9-Deoxy-9-methylene-16,16-difluoro-PGF$_1$, piperadylamide, a prostaglandin analog according to claim 26.

28. A prostaglandin analog according to claim 23, wherein R$_3$ and R$_4$ are both hydrogen.

29. A prostaglandin analog according to claim 28, wherein R$_5$ is methyl.

30. 9-Deoxy-9-methylene-15-methyl-PGF$_1$, piperadylamide, a prostaglandin analog according to claim 29.

31. A prostaglandin analog according to claim 28, wherein R$_5$ is hydrogen.

32. 9-Deoxy-9-methylene-PGF$_1$, piperadylamide, a prostaglandin analog according to claim 31.

* * * * *

UNITED STATES PATENT AND TRADEMARK OFFICE
CERTIFICATE OF CORRECTION

PATENT NO. : 4,145,534
DATED : March 20, 1979
INVENTOR(S) : Gordon L. Bundy

It is certified that error appears in the above–identified patent and that said Letters Patent are hereby corrected as shown below:

IN THE TITLE, "$PFG_1$" should read -- $PGF_1$ --

Column 1, line 68, "-C≡-" should read -- -C≡C- --.

Signed and Sealed this

Thirty-first Day of July 1979

[SEAL]

Attest:

*Attesting Officer*

LUTRELLE F. PARKER
*Acting Commissioner of Patents and Trademarks*